United States Patent [19]

Graf et al.

[11] Patent Number: 4,853,223
[45] Date of Patent: Aug. 1, 1989

[54] CONTROL OF ECTOPARASITES

[75] Inventors: Jean-François Graf, Binningen, Switzerland; Hans W. Hässlin, Grenzach-Wyhlen, Fed. Rep. of Germany; Hessel J. Schuurman, Pfeffingen; Theodor Steiner, Riehen, both of Switzerland; Bruno Wieland, Oakville, Canada

[73] Assignee: Ciba-Geigy Corporation, Ardsley, N.Y.

[21] Appl. No.: 247,972

[22] Filed: Sep. 22, 1988

Related U.S. Application Data

[63] Continuation of Ser. No. 108,346, Oct. 14, 1987, abandoned.

[30] Foreign Application Priority Data

Oct. 23, 1986 [CH] Switzerland ............ 4221/86

[51] Int. Cl.$^4$ ............................................. A01N 25/00
[52] U.S. Cl. ...................................... 424/405; 424/409
[58] Field of Search ......................... 424/490, 405, 409

[56] References Cited

U.S. PATENT DOCUMENTS

| | | | |
|---|---|---|---|
| 3,836,649 | 9/1974 | Telle et al. | 424/203 |
| 4,001,140 | 1/1977 | Foris et al. | 252/316 |
| 4,087,376 | 5/1978 | Foris et al. | 252/316 |
| 4,089,802 | 5/1978 | Foris et al. | 252/316 |
| 4,100,103 | 7/1978 | Foris et al. | 252/316 |
| 4,360,376 | 11/1982 | Koestler et al. | 71/121 |
| 4,460,722 | 7/1984 | Igarashi et al. | 523/206 |
| 4,640,709 | 2/1987 | Beetsman et al. | 71/100 |
| 4,670,250 | 6/1987 | Baker | 424/419 |
| 4,690,786 | 9/1987 | Ninomiya et al. | 264/4.6 |

FOREIGN PATENT DOCUMENTS

| | | |
|---|---|---|
| 0134674 | 3/1985 | European Pat. Off. |
| 0214936 | 3/1987 | European Pat. Off. |
| 2208618 | 8/1984 | Fed. Rep. of Germany |
| 2016925A | 9/1979 | United Kingdom |

OTHER PUBLICATIONS

Veterinary Medicine and Small Animal Clinician, vol. 79, No. 9 (T. L. Fridinger), 1984, pp. 1151-1555.
Span, vol. 27, No. 1, Jan. 1984 (R. N. Brice), pp. 30-32.
Australian Vet. J. 5, 44, 344, 349 (Aug. 1968).
Chemical Abstracts, vol. 81, No. 17, Oct. 28, 1974, p. 151, No. 100692t.

*Primary Examiner*—William R. Dixon, Jr.
*Assistant Examiner*—Andrew Griffis
*Attorney, Agent, or Firm*—Edward McC. Roberts

[57] ABSTRACT

The present invention relates to a method of controlling ectoparasites in domestic animals employing used treatment liquid, in which method animals are passed through animal dips/spray races in which there is an aqueous dispersion of a microencapsulated ectoparasiticide, thus achieving a uniform distribution of the active ingredient between the animals.

13 Claims, No Drawings

CONTROL OF ECTOPARASITES

This is a continuation of application Ser. No. 108,346 filed on Oct. 14, 1987 abandoned.

The present invention relates to a method of controlling ectoparasites in domestic animals that is characterised in detail hereinbelow and that is based on using the parasiticide in microencapsulated form, thereby preventing stripping of the active ingredient.

Many pesticides that are very active per se exhibit undesirable secondary phenomena when used in specific forms of administration, which considerably interfere with their use in animal husbandry. One of these very serious side-effects is the stripping (extraction effect) of ectoparasiticides. This stripping has already been known for some time, see Australian Veterinary Journal, Vol. 44, August, 1968, pages 344 to 349.

The stripping effect is a property that cannot be assigned to any particular class of substances. Rather, representatives of classes of substances that are very different chemically, such as, for example, organophosphates, organochlorine compounds, carbamates, amidines and pyrethroids, exhibit this effect. Commercial products having a pronounced stripping effect are, for example, AMITRAZ=N,N-di-(2,4-xylyliminomethyl)-methylamine; BROMPHOS-ETHYL=O-(4-bromo-2,5-dichlorophenyl)-O,O-diethyl thiophosphate; DIOXATHION=S,S'-(1,4-dioxan-2,3-diyl)-O,O,O',O'-tetraethyl dithiophosphate; PROPETAMPHOS=1-methylethyl-(E)-3-[[(ethylamino)methoxyphosphinothioyl]oxy]-2-butenoic acid ester; CHLORPYRIFOS=thiophosphoric acid O,O-diethyl-O-(3,5,6-trichloro-2-pyridinyl)ester; DIAZINON=thiophosphoric acid O,O-diethyl-O-[6-methyl-2-(1-methylethyl)-4-pyrimidinyl]ester; COUMAPHOS=thiophosphoric acid O-(3-chloro-4-methyl-2-oxo-2H-1-benzopyran-7-yl)-O,O-diethyl ester; ETHION=dithiophosphoric acid S,S'-methylene-O,O,O',O'-tetraethyl ester; MALATHION=[(dimethoxyphosphinothioyl)thio]-succinic acid diethyl ester; CHLORFENVINPHOS=-phosphoric acid 2-chloro-1-(2,4-dichlorophenyl)ethenyl-diethyl ester; TOXAPHENE=chlorinated camphene; LINDANE=$1\alpha,2\beta,3\beta,4\alpha,5\alpha,6\beta$-hexachlorocyclohexane; TIFATOL=N-(2,3-dihydro-3-methyl-1,3-thiazol-2-ylidene)-2,4-xylidine and PHOXIM=O-($\alpha$-cyanobenzylideneamino)-O',O''-diethyl thiophosphate.

The term "stripping" means an undesirable, excessive adsorption of an ectoparasiticide by the coat or skin of a treated animal from a liquid form of application which consequently leads to an over-proportional reduction in the concentration of active ingredient in the remaining liquid.

A quantitative measure of the stripping effect is the stripping rate which is derived from the quotient of the amount of active ingredient actually extracted and the amount of active ingredient theoretically extracted, the amount of active ingredient actually extracted being understood as the amount that has been extracted from the liquid formulation by the treated animal, and the amount of active ingredient theoretically extracted being understood as the amount present, before use of the liquid formulation, in a volume corresponding to the volume extracted by the treated animal. If an animal is passed, for example, through a plunge dip, a certain volume of the liquid formulation stays in the coat or on the skin of the animal. If the concentration in the dip does not then change, a stripping rate of 1 results. This means that the active ingredient does not strip. If, however, the active ingredient has a high affinity for the hair or the skin of the animal, then the animal extracts from the dip more active ingredient than is commensurate with the corresponding volume of liquid, and the stripping rate then becomes greater than 1, that is to say this active ingredient exhibits a stripping effect.

In practice, ectoparasiticides are generally applied to domestic animals, especially to herd animals, such as cattle, sheep, goats, horses, donkeys, camels, pigs, reindeer, caribou and buffalo, but also to animals in smaller groups, such as dogs and rabbits, by bringing the animals into intensive contact with a liquid formulation of the active ingredient. This is normally carried out by passing the animals through plunge dips, spray races, showers or similar systems—hereinafter referred to as dips for the sake of simplicity—, the active ingredient being used in the form of a solution or, predominantly, in the form of an emulsion or dispersion. These will be systems in which, for economic or ecological reasons, treatment liquid that has already been used will be used for the treatment of further animals.

It has been established that, because of their pronounced affinity for the hair or the skin of the animal, very many ectoparasiticides stay on the treated animal to a far greater degree than is commensurate with the amount of liquid absorbed by the coat.

If, for example, several animals are passed one after another through the same plunge dip and if the active ingredient used exhibits a stripping effect (extraction effect), on the one hand a rapid decrease in concentration in the dip liquid is detected and, on the other hand, the first animals extract far more active ingredient from the dip liquid than do the subsequent animals, as a result of which the last animals possibly are not treated adequately.

If overdosing and underdosing are to be avoided, the progressive reduction in concentration of the active ingredient in the dip liquid must be compensated. This means that the operator of the dip is constantly confronted with different dilution rates and top-up quantities. He is forced to measure the actual concentration time and again and to top up with accurately calculated quantities of active ingredient and diluent. In addition, more active ingredient is consumed overall than is necessary for efficient treatment of a domestic animals, which is desirable neither from an economic nor from an ecological standpoint.

The disadvantages of the stripping phenomenon are, therefore, the uneconomical and complicated handling of the animal dips, spray races, showers and other appropriate systems, overdosing and intoxication of the animals treated first and underdosing and, hence, lack of effect in the animals treated last.

Furthermore, in the practical application of animal dips, stripping is one of the main causes of there being no radical success in the treatment against ectoparasites despite the dips. In addition to this, there is the disadvantage often observed with underdosing that some of the parasites survive and come into contact with the active ingredient again, thereby enhancing their resistance, so that whole classes of active ingredient may possibly have to be replaced prematurely by others.

It has now been found that the stripping effect of ectoparasiticides and all the disadvantages resulting therefrom can surprisingly be eliminated completely or substantially completely in a simple manner by using in the animal dips, instead of an active ingredient emulsion or active ingredient dispersion, the ectoparasiticide in microencapsulated form, and therefore the present invention relates especially to the use of microencapsulated ectoparasiticides in animal dips in which used treatment liquid is used for the treatment of further animals.

Within the scope of the present invention, the treatment liquid is referred to as "used" if it has been employed on one or more animal(s). For example, the dip liquid of a plunge dip can be considered to be used in relation to subsequent animals once the first animal is in the dip liquid, i.e. all subsequent animals receive a used treatment liquid. The same applies correspondingly to other apparatus in which, for example, the treatment liquid is collected and re-used.

The present invention therefore relates to a method of controlling ectoparasites in domestic animals, in which method the domestic animals are passed through a dip charged with a dip liquid that contains an ectoparasiticide, and in which method used treatment liquid is used for the treatment of further domestic animals, the method being characterised in that a dip in which there is an aqueous dispersion of a microencapsulated ectoparasiticide is used. The use of microcapsules of from 1 to 30μ, preferably from 1 to 5μ, cross-section has been found to be especially advantageous.

The method can be used especially advantageously if the dips in question are plunge dips, spray races or showers. A method in which the liquid formulation of the active ingredient is applied to the animals in a wetting manner is also advantageous.

The method according to the invention constitutes an improvement in principle whenever the ectoparasiticide to be applied exhibits a stripping rate of greater than 1 when formulated in a conventional manner.

A good parasiticidal action is obtained against ectoparasites, such as, for example, ticks, mites, the causative organisms of myiasis, lice, sheep keds, flies and fleas, when the active ingredient concentration in the dip is from 10 to 1,000 ppm, preferably from 50 to 500 ppm.

Processes for the microencapsulation of active ingredients of different fields of action have long been known to the person skilled in the art, for example from DE-3,417,200; EP-165,227; EP-141,584; U.S. Pat. No. 3,624,248; U.S. Pat. No. 3,492,380; U.S. Pat. No. 4,102,800; U.S. Pat. No. 4,436,719; U.S. Pat. No. 4,497,793; DE-2,910,252; DE-3,207,421; U.S. Pat. No. 4,563,212; DE-2,757,634; U.S. Pat. No. 4,160,838; U.S. Pat. No. 4,285,720; U.S. Pat. No. 4,230,809; U.S. Pat. No. 4,303,548; DE-2,757,528 and EP-214,936, the process for encapsulation being of no consequence for the use according to the invention. The coating of the active ingredient so that its affinity for the coat or skin of the animal is no longer relevant, the size of the capsules and the concentration of the active ingredient in the dip liquid are significant, however.

A preferred embodiment of the method according to the invention comprises using an aqueous dispersion of microencapsulated ectoparasiticides having a capsule wall of polyurea. This dispersion can be prepared by dispersing or emulsifying in water a polyisocyanate and an ectoparasiticide that is sparingly soluble in water, in the presence of an anionic dispersion agent and of a non-ionic protective colloid and/or a non-ionic surfactant, and adding a polyamine to the resulting dispersion or emulsion. This preparation process is described in detail hereinbelow as a preferred process for the preparation of an aqueous dispersion of microencapsulated ectoparasiticides having a capsule wall of polyurea.

Generally suitable anionic dispersion agents are oligomers and polymers and also polycondensates that contain a number of anionic groups sufficient to ensure their water-solubility. Suitable anionic groups are, for example, sulpho groups or carboxy groups, but polymers having carboxy groups can be used only at a relatively high pH value, preferably at a pH value of greater than 5. The number of anionic groups per polymer molecule is, as a rule, at least 60% of the number of monomer units involved in the building of the molecule. Oligomers and polymers containing sulpho groups can be produced either by polymerisation of monomers containing sulpho groups or by sulphonation of the oligomers or polymers in question. Polymers containing carboxy groups can be obtained by hydrolysis of polyacrylates or polymethacrylates, it being necessary for the degree of hydrolysis to be at least 60%. Sulphonated polymers and condensation products of aromatic sulphonic acids with formaldehyde are especially suitable as anionic dispersion agents. Typical examples of such anionic dispersion agents are:

A. salts of polystyrenesulphonic acid, especially the alkali metal, alkaline earth metal and ammonium salts, and the salts of organic amines that can be obtained by polymerisation of styrenesulphonic acid or the salts thereof or by sulphonation of polystyrene and subsequent neutralisation with an appropriate base; in the case of the sulphonation of polystyrene the degree of sulphonation should be at least 60%;

B. salts of polyvinylsulphonic acid, especially the alkali metal, alkaline earth metal and ammonium salts, and the salts with organic amines that can be manufactured by polymerisation of vinylsulphonic acid or the salts thereof;

C. salts of condensation products of naphthalenesulphonic acids, especially naphthalene-2-sulphonic acid, with formaldehyde, especially the alkali metal, alkaline earth metal and ammonium salts, and their salts with organic amines that can be obtained by sulphonation of naphthalene, condensation of the resulting naphthalenesulphonic acids with formaldehyde and neutralisation with an appropriate base. The condensation products can be described by the formula

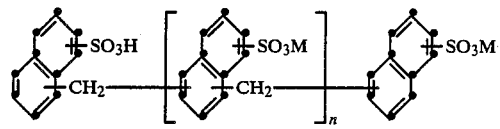

in which M represents sodium, potassium, magnesium, calcium, ammonium or the cation derived from an organic amine and n represents 1–25. The molecular weight of these products is about 500–6000;

D. salts of condensation products of naphthalenesulphonic acid with phenolsulphonic acid and formaldehyde, especially the alkali metal, alkaline earth metal and ammonium salts, and the salts with organic amines. These products are polymers containing sulpho groups, which have an average molecular weight of 6,000–8,000 and in which the monomeric units naphthalene and phenol are bonded to each other in some cases via methylene groups and in some cases via sulphone groups. Their structure is approximately as follows:

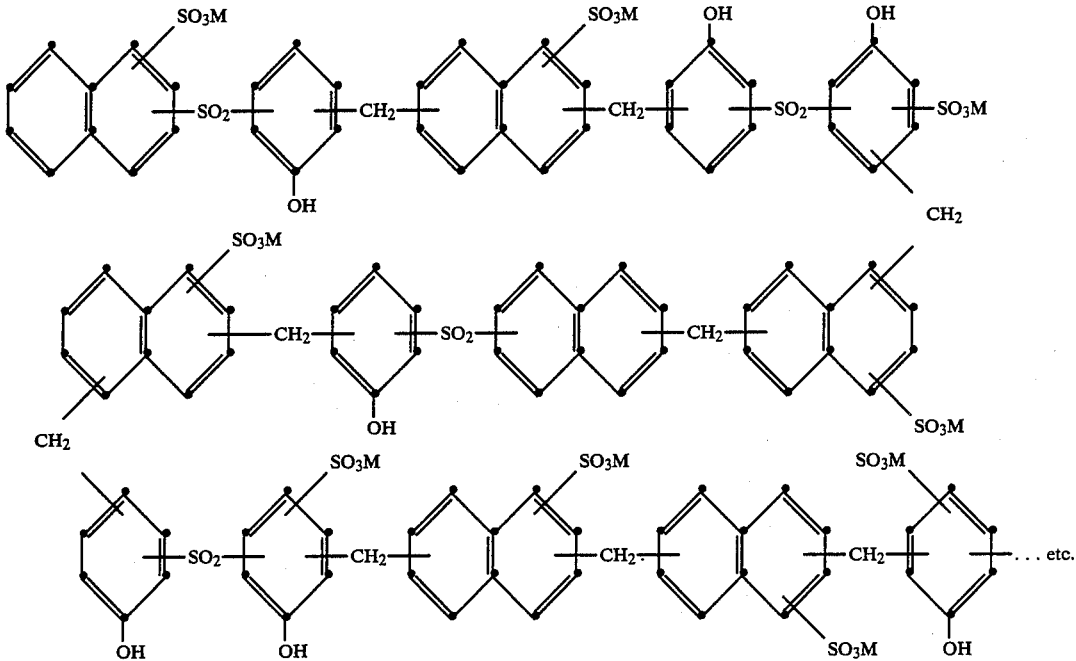

wherein M represents sodium, potassium, magnesium, calcium, ammonium or the cation derived from an organic amine.

E. salts of lignosulphonic acid, especially the sodium, potassium, magnesium, calcium or ammonium salts.

Preferred anionic dispersion agents are salts of polystyrenesulphonic acid (type A), salts of condensation products of naphthalenesulphonic acid with formaldehyde (type C) and especially condensation products of naphthalenesulphonic acid with phenolsulphonic acid and formaldehyde (type D).

The condensation products of naphthalenesulphonic acid with phenolsulphonic acid and formaldehyde of the above-mentioned type D, which are especially preferred as anionic dispersion agents, have not hitherto been described in the literature. They can be manufactured by first converting naphthalene at 120°–130° C. into naphthalenesulphonic acid with concentrated sulphuric acid and/or oleum, then adding phenol to the reaction mixture and first reacting further at 120°–130° and then removing the water of reaction in vacuo at 150°–170° C. and, after cooling to 90°–100°, condensing the reaction product with formaldehyde, then neutralising to pH 6–7, concentrating to dryness by evaporation and granulating the residue. In this manner, a water-soluble anionic dispersion agent (hereinafter referred to as "dispersion agent A") is obtained in the form of a granulate having an average molecular weight of 6,000–8,000.

In the sulphonation of naphthalene under the conditions mentioned above, naphthalene-2-sulphonic acid is predominantly formed together with small quantities of naphthalenedisulphonic acid. After the phenol has been added it too is sulphonated. In this case, however, especially during subsequent heating at 150°–170°, sulphones, such as 4,4'-dihydroxydiphenylsulphone and 4-hydroxyphenylnaphthylsulphone, are formed on a considerable scale in addition to the phenolsulphonic acid. For this reason, upon subsequent condensation with formaldehyde, there is produced a polymer in which the monomeric units naphthalene and phenol are linked in some cases via methylene groups and in some cases via sulphone groups. In the manufacture of dispersion agent A, naphthalene, phenol, sulphuric acid, formaldehyde and base can be used in a molar ratio of 1:(0.5 to 1):(2 to 2.5):(0.4 to 0.8):(2 to 3). Preferably, the molar ratio of naphthalene:phenol:sulphuric acid:formaldehyde:base will be 1:(0.7):(2):(0.5):(2), sodium hydroxide advantageously being used as the base. The sulphuric acid will advantageously consist of mixtures of concentrated sulphuric acid and oleum, the amount of free $SO_3$ in the oleum being at least equivalent to the amount of water in the concentrated sulphuric acid so that, when concentrated sulphuric acid and oleum are mixed, at least 100% strength sulphuric acid is produced. Formaldehyde is advantageously used in the form of an aqueous solution, for example a 37% aqueous solution. The removal of the water of reaction by distillation is advantageously carried out under a pressure of 10–50 mbar.

Generally suitable non-ionic protective colloids are water-soluble polymers of which the molecular weight is, as a rule, 10,000 to 200,000. The mean diameter of the capsules formed can be influenced by way of the molecular weight of the water-soluble polymer used in each case. The use of water-soluble polymers having a lower molecular weight results in a lower viscosity of the reaction mixture and, therewith, in the formation of larger capsules, whilst the use of water-soluble polymers having a higher molecular weight causes higher viscosity of the reaction mixture and, therewith, the formation of capsules of smaller diameter. Suitable water-soluble polymers are, for example: polyvinyl alcohol, polyvinyl methyl ether, polyvinylpyrrolidone, hydroxyethylcellulose, hydroxypropylcellulose, methylcellulose (degree of substitution: 1.5 to 2), hydroxyethylmethylcellulose, hydroxypropylmethyl-cellulose, poly-(2-hydroxyethyl)-methacrylate, poly-[2-(2-hydroxyethoxy)-ethyl]-methacrylate, polyethylene oxide (polyoxyethylene) and polyallyl alcohol (polyglycidol).

A preferred non-ionic protective colloid is polyvinyl alcohol. Especially suitable are polyvinyl alcohols having a viscosity of 4–60 cP (measured in 4% aqueous solutions at 20° C.) that have been manufactured by hydrolysis of polyvinyl acetate, the degree of hydrolysis being at least 60%, preferably, however, 80–95%. Suitable products of this type are available commercially, for example under the name MOWIOL ®.

Generally suitable non-ionic surfactants are non-ionic water-soluble polymers having a molecular weight below 20,000, preferably below 5,000. Especially suitable non-ionic surfactants of this type are those products that can be manufactured by reaction of ethylene oxide or by combined reaction of ethylene oxide and propylene oxide with fatty alcohols, alkylphenols, fatty acids, fatty acid esters of polyhydroxy compounds, fatty acid amides and fatty amines, it being possible for the number of ethylene oxide and propylene oxide units to be varied within the wide limits. Generally, the number of ethylene oxide or ethylene oxide/propylene oxide units is 1–200, preferably 5–100 and especially 8–40. Suitable non-ionic surfactants are, for example:

alkylpolyethylene glycol ethers of the formula

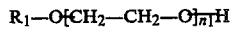

wherein $R_1$ represents $C_8$–$C_{20}$-alkyl and $n_1$ represents 2–100. Products of this type are available commercially, for example under the names BRIJ ® (Atlas Chemical), ETHYLAN ® CD and ETHYLAN ® D (Diamond Shamrock), GENAPOL ® C, GENAPOL ® O and GENAPOL ® S (Hoechst AG);

alkylphenolpolyethylene glycol ethers of the formula

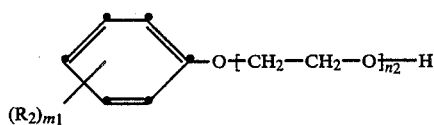

wherein $R_2$ represents $C_8$–$C_{12}$-alkyl, $m_1$ represents 1–3 and $n_2$ represents 2–40. Preferred meanings of $R_2$ are octyl and nonyl. Products of this type are available commercially, for example under the names Antarox (GAF), TRITON ® X (Röhm & Haas Co.), AT-LOX ® 4991 (ICI), ARKOPAL ® N (American Hoechst) and ETHYLAN ® (Lankro Chem. Ltd);

α-phenethylphenol polyglycol ethers of the formula

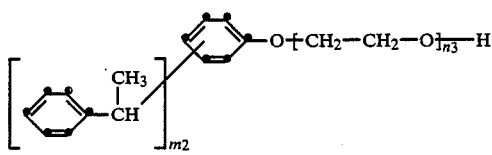

wherein $m_2$ represents 1–3 and $n_3$ represents 5–40. These products are also called ethoxylated styrylphenols. Products of this type that are available commercially are, for example, DISTY ® 125 (Geronazzo) and SO-PROPHOR ® CY 18 (Rhone Poulenc S.A.);

fatty acid (polyethoxyethyl) esters of the formula

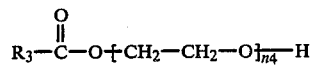

wherein $R_3$ represents $C_8$–$C_{22}$-alkyl or $C_{10}$–$C_{22}$-alkenyl and $n_4$ represents 2–50. These products are derived especially from lauric acid, oleic acid and stearic acid. Such products are available commercially, for example under the names NONISOL ® (Ciba-Geigy) or MYRJ ® (ICI);

sorbitan polyethylene glycol ether fatty acid esters of the formula

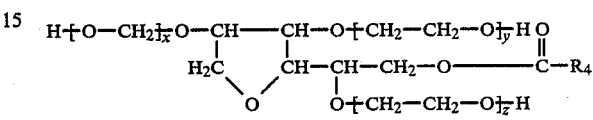

wherein $R_4$ represents $C_8$–$C_{20}$-alkyl and each of x, y and z represents 1–50, the sum of $x+y+z$ being 20–150. As acid radicals $R_4$ there come into consideration especially the radicals of lauric acid, stearic acid, palmitic acid and oleic acid. Such products are also called polysorbates and are available commercially, for example under the name TWEEN ® (ICI);

triglyceride polyethylene glycol ethers of the formula

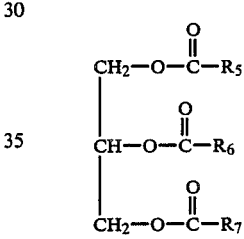

in which each of $R_5$, $R_6$ and $R_7$ represents the radical of the formula

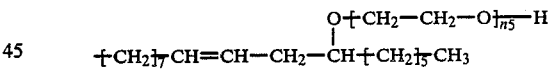

and each of $R_5$ and $R_6$, independently of the other, also represents $C_8$–$C_{20}$-alkyl or $C_8$–$C_{20}$-alkenyl, $n_5$ representing 3–100. As acid radicals $R_5CO$— and $R_6CO$— having $C_8$–$C_{20}$-alkyl and $C_8$–$C_{20}$-alkenyl groups there come into consideration especially the radicals of lauric acid, palmitic acid, stearic acid and oleic acid. A preferred representative of this surfactant type is ethoxylated castor oil. Such products are available commercially under the name EMULSOGEN ® (Hoechst AG);

fatty acid polyethoxyethylamides of the formula

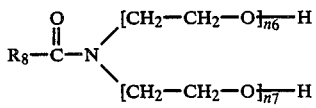

wherein $R_8$ represents $C_8$–$C_{20}$-alkyl or $C_8$–$C_{20}$-alkenyl and $n_6$ and $n_7$ each represents 1–25. As acid radicals $R_8CO$— there come into consideration especially the radicals of lauric acid, oleic acid, palmitic acid and stearic acid. Products of this type are available commercially, for example under the names AMIDOX ® (Stepan Chemical Co.), ETHOMID ® (Armak Co.);

N-polyethoxyethylamines of the formula

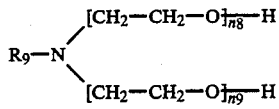

wherein $R_9$ represents $C_8$–$C_{18}$-alkyl or $C_8$–$C_{18}$-alkenyl and $n_8$ represents in each case 1–15. Especially suitable are the products derived from fatty amines, such as coconut fatty amine, oleylamine, stearylamine and tallow fatty amine. Such products are available commercially, for example under the name GENAMIN ® (Hoechst); N,N,N',N'-tetra(polyethoxypolypropoxyethyl)-ethylenediamines of the formula

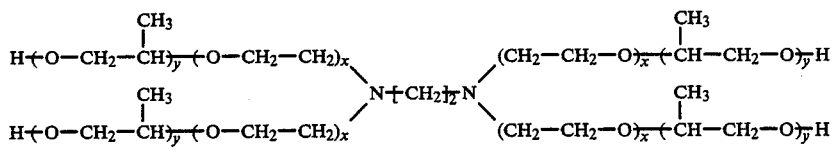

wherein each of x and y represents 2–50 and the sum of x+y is in each case 4–100. Products of this type are available commercially, especially under the names TERRONIL ® and TETRONIC ® (BASF Wyandotte Corp.);

alkyl-polyethylene glycol/polypropylene glycol ethers of the formula

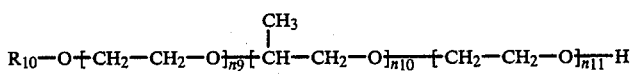

wherein $R_{10}$ represents hydrogen, $C_8$–$C_{20}$-alkyl or $C_8$–$C_{20}$-alkenyl and each of $n_9$ and $n_{11}$ represents 2–200 and $n_{10}$ represents 10–80 and the sum of $n_9+n_{10}+n_{11}$ is 15–450. Especially suitable products of this type are, for example, the polyethylene oxide/polypropylene oxide block polymers ($R_{10}$=H) available commercially under the name PLURONIC ® (BASF Wyandotte Corp.)

Preferred non-ionic surfactants are ethylene oxide/propylene oxide block polymers (PLURONICS ®), N,N,N',N'-tetra(polyethoxypolypropoxyethyl)-ethylenediamines (TETRONICS ®), nonylphenol polyglycol ethers having 10–20 ethylene oxide units, alkylpolyethylene glycol ethers derived from fatty alcohols (GENAPOL ®) and N-polyethoxyethylamines derived from fatty amines (GENAMIN ®). Especially preferred non-ionic surfactants are ethylene oxide/propylene oxide block polymers (PLURONICS ®).

The term "polyisocyanates" is generally to be understood within the scope of the present Application as those compounds that contain two or more isocyanate groups in the molecule. Preferred are di- and tri- isocyanates, it being possible for the isocyanate groups to be bonded to an aliphatic or an aromatic structure. Examples of suitable aliphatic diisocyanates are tetramethylene diisocyanate, pentamethylene diisocyanate and hexamethylene diisocyanate. Suitable aromatic isocyanates are toluylene diisocyanate (TDI; mixture of 2,4- and 2,6-isomers), diphenylmethane-4,4'-diisocyanate (MDI; DESMODUR ® VL (Bayer)), polymethylenepolyphenyl isocyanate (MONDUR ® MR (Mobay Chemical Company)); PAPI ®, PAPI ® 135 (Upjohn Co.), 2,4,4'-diphenyl ether triisocyanate, 3,3'-dimethyl-4,4'-diphenyl diisocyanate, 3,3'-dimethoxy-4,4'-diphenyl diisocyanate, 1,5-naphthylene diisocyanate and 4,4',4''-triphenylmethane triisocyanate. Another suitable diisocyanate is isophorone diisocyanate. Also suitable are addition products of diisocyanates to polyhydric alcohols, such as ethylene glycol, glycerol and trimethylolpropane, there being added per mole of polyhydric alcohol in each case the number of moles of diisocyanate corresponding to the number of hydroxy groups of the particular alcohol. In this manner, several molecules of diisocyanate are bonded via urethane groups to the polyhydric alcohol to form higher molecular weight polyisocyanates. An especially suitable product of this type can be manufactured by reacting 3 moles of toluylene diisocyanate with one mole of 2-ethylglycerol (1,1-bis-methylolpropanol) (DESMODUR ® L). Other suitable products are obtained by addition of hexamethylene diisocyanate or isophorone diisocyanate to ethylene glycol or glycerol. Preferred polyisocyanates are diphenylmethane-4,4'-diisocyanate and polymethylenepolyphenyl isocyanate.

The above-mentioned di- and tri-isocyanates can each be used on their own or in the form of mixtures of two or more of those isocyanates.

The term "polyamines" is generally to be understood within the scope of the present invention as those compounds containing two or more amino groups in the molecule, it being possible for these amino groups to be bonded to aliphatic and aromatic structures. Suitable aliphatic polyamines are, for example, α,ω-diamines of the formula

wherein n represents an integer of 2–6. Examples of such diamines that may be mentioned are ethylenediamine, propylene-1,3-diamine, tetramethylenediamine, pentamethylenediamine and hexamethylenediamine. A preferred diamine is hexamethylenediamine.

Other suitable aliphatic polyamines are polyethyleneimines of the formula

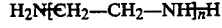

wherein n represents an integer of 2–5. Examples of such polyethyleneimines that may be mentioned are diethylenetriamine, triethylenetetramine, tetraethylenepentamine and pentaethylenehexamine.

Other suitable aliphatic polyamines are dioxaalkane-α,ω-diamines, such as 4,9-dioxadodecane-1,12-diamine of the formula

Suitable aromatic polyamines are, for example, 1,3-phenylenediamine, 2,4-toluylenediamine, 4,4'-diaminodiphenylmethane, 1,5-diaminonaphthalene, 1,3,5-triaminobenzene, 2,4,6-triaminotoluene, 1,3,6-triaminonaphthalene, 2,4,4'-triaminodiphenyl ether, 3,4,5-triamino-1,2,4-triazole and 1,4,5,8-tetraaminoanthraquinone. Those of the above-mentioned polyamines which are not, or not sufficiently, water-soluble can be used in the form of hydrochlorides.

Aslo suitable are polyamines that contain, in addition to the amino groups, sulpho groups or carboxy groups. Examples of such polyamines are 1,4-phenylenediaminesulphonic acid, 4,4'-diaminodiphenyl-2-sulphonic acid, or diaminomonocarboxylic acids, such as ornithine and lysine.

The above-mentioned polyamines can be used on their own or in the form of mixtures of two or more polyamines.

The ectopesticides that generally come into consideration and that can be formulated according to the preferred process are those which
 are insoluble in water, but are stable towards water,
 are liquid at room temperature or have a melting point of $\leq 60°$ C. or those which are soluble in a water-immiscible organic solvent,
 are inert towards isocyanates and
 have the capacity to dissolve polyisocyanates of the above-mentioned type.

Suitable water-immiscible solvents in which the ectopesticides can be dissolved are aliphatic and aromatic hydrocarbons, such as hexane, cyclohexane, benzene, toluene, xylene, mineral oil or kerosene. Also suitable are cyclohexanone and halogenated hydrocarbons, such as methylene chloride, chloroform, carbon tetrachloride, chlorobenzene and o-dichlorobenzene. Mixtures of mono- and poly-alkylated aromatic compounds, such as, for example, those available commercially under the name (SHELLSOL®), are also suitable.

The preferred preparation process is suitable in principle for all ectoparasiticides, irrespective of their chemical structure, that exhibit a stripping effect in aqueous formulations.

Examples of such types of active ingredient were described at the beginning.

The microcapsules may contain one or several active ingredients(s).

The process for the preparation of microcapsules that is classified as preferred is advantageously carried out by first dissolving the anionic dispersion agent and the non-ionic protective colloid and/or the non-ionic surfactant in water and then adding a solution of one or more polyisocyanates of the above-mentioned type in one or more of the above-mentioned pesticidal active ingredients or in a solution of one or more of those active ingredients in a water-immiscible solvent, and intensively stirring the mixture until a homogeneous dispersion is obtained. While continuing to stir the mixture, one or more polyamines of the above-mentioned type are then added and the mixture is stirred further until the polyamine has reacted completely with the isocyanate. The polyamines are advantageously added in the form of aqueous solutions.

The encapsulation process can be carried out at room temperature or at moderately elevated temperature. Suitable temperatures are in the range of from 10 to 75° C. Preferably, the process according to the invention is carried out in a temperature range of from 20° to 45° C.

The reaction times of the polyisocyanate with the polyamine are, as a rule, from 2 to 30 minutes. The respective degree of reaction and the end of the reaction can be determined by titration of the free amine present in the aqueous phase.

The components required for forming the capsule wall can generally be used in a quantity of from 2.5 to 30% by weight, preferably from 5 to 20% by weight, based on the material to be encapsulated. The material to be encapsulated may consist of one active ingredient, or of a mixture of two or more active ingredients, or of a solution of one active ingredient or a mixture of two or more active ingredients in a water-immiscible solvent. The quantity of the components required for forming the capsule wall in any one case depends especially on the thickness of the wall of the capsules to be prepared and also on the size of capsules.

According to the preferred preparation process, aqueous suspensions of microcapsules can be prepared, that contain, per liter, from 100 to 700 g of microcapsules. Preferably, the suspensions that can be prepared according to this process will contain from 400 to 600 g of microcapsules per liter.

The suspensions of microcapsules that can be prepared according to the preferred preparation process are immediately ready for use. They may, however, be stabilised by further additives, such as surfactants, thickeners, anti-foams and anti-freeze agents, for transport and storage.

It is, however, also possible to separate the microcapsules by filtration or centrifugation from the suspension that is obtained directly, and either to dry them or to convert them into a suspension again. The microcapsules that have been separated from the suspension and dried are in the form of a flowable powder of virtually unlimited storage life.

As a result of the simultaneous use of an anionic dispersion agent and a non-ionic protective colloid and/or a non-ionic surfactant in the preferred preparation process, when the solution of the polyisocyanate is dispersed in the pesticidal active ingredient, there is avoided the sharp increase in viscosity that occurs especially when an anionic dispersion agent, such as lignosulphonate, is used on its own. Not only does this make it easier to carry out the process but, at the same time, more rapid and more complete reaction of the polyisocyanate and the polyamine is achieved which largely prevents the formation of undesirable by-products. As a result of reducing the viscosity of the reaction mixture a finer dispersion is achieved with the same shearing force and, therewith, a reduction in the diameter of the capsules produced. The capsule suspensions prepared in this manner are stable and exhibit no sediment formation even in the case of prolonged storage. The suspensions of microcapsules that can be prepared also exhibit thixotropic properties if suitable types and quantities of anionic and non-ionic dispersion agents are chosen, and can, therefore, be brought into a readily flowable state in a simple manner by shaking or by stirring.

In the following Examples which illustrate the preferred process in detail, the trade names used and other terms that are not self-evident denote the following products:

ANIONIC DISPERSION AGENTS

Dispersion agent A: sodium salt of a condensation product of naphthalenesulphonic acid with phenolsulphonic acid and formaldehyde manufactured according to Example 1.

TAMOL ® SN: sodium salt of a condensation product of naphthalenesulphonic acid and formaldehyde, manufacturer: Röhm & Haas Co.

NON-IONIC DISPERSION AGENTS (PROTECTIVE COLLOIDS)

MOWIOL ® 18-88: polyvinyl alcohol having a viscosity of 18 cP (measured in a 4% aqueous solution at 20° C.), manufactured by hydrolysing polyvinyl acetate (degree of hydrolysis: 88%), manufacturer: Hoechst AG.

MOWIOL ® 40-88: polyvinyl alcohol having a viscosity of 40 cP (measured in a 4% aqueous solution at 20° C.), manufactured by hydrolysing polyvinyl acetate (degree of hydrolysis: 88%), manufacturer: Hoechst AG.

NON-IONIC SURFACTANTS

PLURONIC ® F-108: ethylene oxide/propylene oxide block polymer of the formula $(EO)_x-(PO)_y-(EO)_z$ having a molecular weight of approximately 16,000 and an ethylene oxide content of 80%, manufacturer: BASF Wyandotte Corp.

PLURONIC ® P-85: ethylene oxide/propylene oxide polymer of the formula $(EO)_x-(PO)_y-(EO)_z$ having a molecular weight of 4500 and an ethylene oxide content of 50%, manufacturer: BASF Wyandotte Corp.

PLURONIC ® L-42: ethylene oxide/propylene oxide block polymer of the formula $(EO)_x-(PO)_y-(EO)_z$ having a molecular weight of 1450 and an ethylene oxide content of 20%, manufacturer: BASF Wyandotte Corp.

TETRONIC ® 707: ethoxylated/propoxylated ethylenediamine having a molecular weight of 12,000 and an ethylene oxide content of 70%, manufacturer: BASF Wyandotte Corp.

ANTAROX ® CO 710: nonylphenolpolyglycol ether having 10 ethylene oxide units, manufacturer: GAF GENAPOL ® C-200: ethoxylated coconut fatty alcohol having 25 ethylene oxide units, manufacturer: Hoechst AG.

GENAMIN ® T100: ethoxylated tallow fatty amine having 10 ethylene oxide units, manufacturer: Hoechst AG

SOLVENT

SHELLSOL ® AB: mixture of mono- and polyalkylated aromatic hydrocarbons, manufacturer: Shell.

EXAMPLE 1

Preparation of dispersion agent A starting materials: 288 g (2.25 mol) of naphthalene; 144 g (1.53 mol) of phenol; 440 g (4.48 mol) of 100% sulphuric acid; 78.5 g (0.97 mol) of 37% aqueous formaldehyde solution; 370 g (4.4 mol) of 48% aqueous sodium hydroxide solution.

The naphthalene is melted in a stirring vessel and, after the addition of the sulphuric acid, the mixture is heated for 4 hours at 120°-125° C. The phenol is then added and the temperature is maintained at 120°-125° C. for a further hour. The reaction vessel is then evacuated to a pressure of 15 mbar, and the temperature is slowly increased to 160° C. and kept there for 3 hours, the water of reaction being removed by distillation. The reaction mixture is then cooled to 105°-110° C. and homogenised by stirring. It is then cooled to 90° C. by cautiously adding 200 g of ice while the homogeneity of the mixture is maintained by constant stirring. The formaldehyde solution is then added over a period of one hour at 90°-95° C. and stirring is then carried out for 3 hours at 95° C. A sample of the reaction mixture then forms with water a clear 5% solution and no longer smells of formaldehyde. The reaction mixture is then cooled to 80° C. by adding 60 g of ice and 60 g of water. After the addition of a further 180 ml of water, the reaction mixture is neutralised at a temperature of 80° C. with approximately 230-250 ml of 48% sodium hydroxide solution. The pH value of a 10% solution of a sample of the reaction mixture is then approximately 6.5. The reaction mixture is then concentrated to dryness by evaporation in vacuo and granulated. In this manner, 900 g of dispersion agent A in the form of a water-soluble granulate are obtained.

PREPARATION OF MICROCAPSULE SUSPENSIONS

EXAMPLE 2

In a 2 liter beaker glass, a solution of 87 g of diphenylmethane-4,4'-diisocyanate in 1080 g of Diazinon is dispersed using a rapid stirrer in a solution of 9.0 g of dispersion agent A and 9.0 g of MOWIOL ® 18-88 (in the form of a 10% aqueous solution) in 392 g of water. After approximately 1 minute, 38 g of hexamethylenediamine (in the form of a 40 % aqueous solution) are added, the temperature rising by 5°-8° C. Stirring is then carried out for one hour and the resulting capsule suspension is stabilised by the addition of a solution of 29 g of GENAMIN ® T 100 in 80 g of water. A stable capsule suspension having a viscosity of 700-1200 cP and a mean particle size of 2-5 μm is obtained.

The ratio of the dispersion agent to MOWIOL ® 18-88 can be varied in the range of from 3:1 to 1:3 with the quality of the suspension of microcapsules formed remaining virtually the same.

EXAMPLE 3

A solution of 18 g of diphenylmethane-4,4'-diisocyanate in 96 g of chlorofenvinphos is dispersed while stirring intensively at room temperature in a solution of 1.6 g of dispersion agent A and 1.6 g of PLURONIC ® F 108 in b 50.5 g of water. 7.4 g of hexamethylenediamine (in the form of a 40% aqueous solution) are then added, the temperature rising by 20°-30° C. The mixture is then stirred until it has cooled to room temperature. A stable low viscosity suspension of microcapsules (viscosity=150 cP) having a mean particle size of 2-3 μm, an active ingredient content of 51.5% by weight and a capsule wall content of 13.6% by weight is obtained.

EXAMPLE 4

A solution of 87 g of diphenylmethane-4,4'-diisocyanate in 1080 g of Diazinon is dispersed while stirring intensively at room temperature in a solution of 9.0 g of dispersion agent A, 3.0 g of MOWIOL ®18-88 (in the form of a 10% aqueous solution) and 6.0 g of PLURONIC ® F 108 in 446 g of water. 37.9 g of hexamethylenediamine (in the form of a 40% aqueous solution) are then added, the temperature rising by 3°-5° C. The resulting liquid suspension of microcapsules having a mean capsule size of 1.5-2.5 μm has a viscosity of 250-600 cP. It contains 61.6% by weight active ingredient and 7.1% by weight capsule wall.

ACTIVITY TEST

EXAMPLE 5

Determination of the stripping rate of DIAZINON, CHLORFENVINPHOS and TIFATOL on sheep's wool (a) These laboratory tests are each carried out with 8-12 g of uncleaned wool from one sheep. For these tests, dips are used that contain Diazinon in the same concentration but that have been prepared with different formulations. One ball of wool is immersed in each of the dips until completely wet through and is then laid on wire mesh so that excess liquid formulation can drop back into the dip in question. The amount of liquid absorbed by the wool and the active ingredient concentration of the liquid formulation remaining in the dip are then measured. The tests are repeated using the same active ingredient concentrations with new wool samples in each case. The stripping rate SR is determined in accordance with the definition described at the beginning. The results are given below.

(a) Results for DIAZINON:

| classical formulation | microencapsulated active ingredient |
| --- | --- |
| 60% DIAZINON<br>3% vaseline oil<br>3% epichlorohydrin<br>1% coumarone resin<br>33% Triton X-100<br>in the form of an aqueous emulsion | DIAZINON is microencapsulated according to Example 2 and the resulting aqueous dispersion is diluted with water accordingly |
| reduction in the active ingredient concentration in the dip<br>19 to 32%<br>stripping rate<br>4.2 to 8.5 | reduction in the active ingredient concentration in the dip<br><3%<br>stripping rate<br>1.0 |

(b) analogous tests with CHLORFENVINPHOS gave the following results:

| stripping rate<br>3.4 to 24.8 | stripping rate<br>2 |
| --- | --- |

(c) analogous tests with Tifatol gave the following results:

| stripping rate<br>3.8 | stripping rate<br>1.5 |
| --- | --- |

EXAMPLE 6

Determination of the stripping rate of DIAZINON in sheep 3 groups each containing 5 sheep are passed through a dip containing the classical aqueous DIAZINON formulation mentioned in Example 5. The stripping rate is determined, as described at the beginning, from the reduction in the volume of the dip liquid and from the active ingredient concentrations before and after use of the dip. In the case of the classical formulation, the stripping rate is between 7.9 and 9.4. Subsequently, 3 groups each containing 5 sheep are passed through a dip containing an identical starting concentration of active ingredient to that in the case of the classical formulation, but in microencapsulated form according to Example 3. The stripping rate in the case of microencapsulated DIAZINON is then 1.0 to 1.5.

These results are being fully corroborated under practical conditions in a field test in Great Britain.

EXAMPLE 7

Determination of the stripping rate of Diazinon in sheep 111 one year old lambs of the Beulah Speckled Face breed each weighing approximately 30 kg and having a complete fleece are passed through a plunge dip system charged with 1,407 liters of a plunge dip that contains a microencapsulated Diazinon formulation according to Example 2, the concentration if Diazinon being 250 ppm (mg/liter). Each sheep stays in the dip for at least one minute. The reduction in dip liquid in the system is compensated by the addition of further dip liquid, the added dip liquid having the same composition as that of the original dip liquid before introduction of the sheep (the added dip liquid similarly contains, therefore, 250 ppm Diazinon). While passing the animals through, samples are taken periodically from the plunge dip which reveal that the Diazinon concentration in the dip is in range of from 227 to 250 ppm, that is to say it remains substantially constant. Measurements of the drop-off liquid of individual sheep also reveal that the Diazinon concentration here is in the range of from 243 to 247 ppm. In this case also, the narrow range of variation in the Diazinon values shows that there is virtually no stripping effect with the microencapsulated Diazinon.

The advantage of using microencapsulated ectoparasiticides in animal dips in which treatment liquid that has already been used is used to treat further animals is thus obvious: since it is necessary for the operator of the dip merely to add more dip liquid containing a quantity of active ingredient corresponding to the initial concentration in order to restore the original volume of dip liquid, continual measuring and constant readjustment of the active ingredient concentration as the animals are passed through can therefore be omitted, which considerably simplifies the procedure and considerably reduces the risk of incorrect dosing and the attendant harm caused to animals that have not been properly treated.

EXAMPLE 8

Action of microencapsulated Diazinon against *Lucilia cuprina* and *Lucilia sericata*

32 sheep having wool 3 to 5 cm in length are treated with the liquid formulation of microencapsulated Diazinon according to Example 2, the concentration of Diazinon being 250 ppm (mg/liter). The liquid formulation is applied to the backs of the sheep at a rate of 3 to 4 liters per sheep using a spray gun.

14 days after the treatment, implants containing clutches of eggs of *Lucilia cuprina* (Diazinon-resistant) and of *Lucilia sericata* are applied to the backs of the sheep, 16 sheep being implanted with *L. cuprina* and 16 sheep with *L. sericata*. Sheep that have been implanted in the same manner but that have not received any Diazinon treatment are used as a control. Implantation is repeated in all the sheep at weekly intervals. 24 and 28 hours after each implantation, a check is made as to whether any living Lucilia larvae are present. The test reveals that, in the control sheep, larval development is taking place while the sheep treated with Diazinon remain free of larvae over a long period. Thus, in the sheep implanted with *Lucilia cuprina* the protective action of the Diazinon lasts for 7 to 8 weeks and, in the sheep implanted with *Lucilia sericata*, for at least 12 weeks.

EXAMPLE 9

Action of microencapsulated Diazinon against *Psoroptes ovis*

4 unshorn sheep each weighing approximately 30 kg are infested with *Psoroptes ovis* by arranging in the fleece of the sheep a wad of wool containing from 15 to 20 scab mites of the species *Psoroptes ovis* at two places, approximately 20 cm apart, on the backs of the sheep. 4 to 5 weeks after infestation, the sheep are sheared and the size of the damaged area of the skin is measured. The affected sheep are then treated with a liquid formulation of microencapsulated Diazinon according to Example 2, two sheep being treated with a liquid formulation containing 250 ppm Diazinon and two sheep being treated with a liquid formulation containing 125 ppm Diazinon (mg/liter). Treatment is carried out by topical application of the liquid formulation, using an ink brush, to the damaged areas of skin and the immediate surroundings. The condition of the treated areas is examined at weekly intervals. Treatment of the damaged animals with microencapsulated Diazinon results in complete healing of the damage in a period of 37 days.

EXAMPLE 10

Action of microencapsulated Diazinon against *Damalinia ovis*

Merino sheep of various ages that have been attacked by *Damalinia ovis* are sheared and sprayed with a liquid formulation of microencapsulated Diazinon according to Example 2, application being carried out simultaneously from above and from below. Every 5 sheep are sprayed with one of the following Diazinon concentrations: 25 ppm, 110 ppm and 240 ppm (mg/liter). One week after treatment, a mortality rate of the lice of 99% is achieved at a concentration of 25 ppm Diazinon, and complete mortality of the lice at the other concentrations. In all cases, the Diazinon action is fully maintained for a further 7 weeks.

We claim:

1. A method of controlling ectoparasites in domestic animals, in which method the domestic animals are passes through a dip charged with a dip liquid that contains an ectoparasiticide, and in which method used treatment liquid is utilized for the treatment of further domestic animals, characterized in that a dip in which there is an aqueous dispersion of a microencapsulated ectoparasiticide is utilized.

2. A method according to claim 1, characterised in that the dip in question is a plunge dip, a spray race or a shower.

3. A method according to claim 1, characterised in that the microcapsules have a cross-section of from 1 to 30μ.

4. A method according to claim 3, characterised in that the microcapsules have a cross-section of from 1 to 5μ.

5. A method according to claim 1, characterised in that the dip liquid contains the active ingredient in a concentration of from 10 to 1,000 ppm.

6. A method according to claim 5, characterised in that the dip liquid contains the active ingredient in a concentration of from 50 to 500 ppm.

7. A method according to claim 1, characterised in that an aqueous dispersion of a microencapsulated ectoparasiticide having a capsule wall of polyurea is utilized.

8. A method according to claim 7, characterised in that as the aqueous dispersion of a microencapsulated ectoparasiticide having a capsule wall of polyurea there is utilized one that has been prepared by dispersing or emulsifying in water a polyisocyanate and an ectoparasiticide that is sparingly soluble in water, in the presence of an anionic dispersion agent and at least one non-ionic protective colloid and/or a non-ionic surfactant, and adding a polyamine to the resulting dispersion or emulsion.

9. A method according to claim 1, characterised in that there is utilized as the ectoparasiticide an active ingredient selected from the classes of substances comprising organophosphates, organochlorine compounds, carbamates, amidines and pyrethroids.

10. A method according to claim 9, characterised in that the selected active ingredient is N,N-di-(2,4-xylyliminomethyl)-methylamine; O-(4-bromo-2,5-dichlorophenyl)-O,O-diethyl thiophosphate; S,S'-(1,4-dioxan-2,3-diyl)-O,O,O',O'-tetraethyl dithiophosphate; 1-methylethyl-(E)-3-[[(ethylamino)-methoxyphosphinothioyl]oxy]-2-butenoic acid ester; thiophosphoric acid O,O-diethyl-O-(3,5,6-trichloro-2-pyridinyl)ester; thiophosphoric acid O,O-diethyl-O-[6-methyl-2-(1-methylethyl)-4-pyrimidinyl]ester; thiophosphoric acid O-(3-chloro-4-methyl-2-oxo-2H-1-benzopyran-7-yl)-O,O-diethyl ester; dithiophosphoric acid S,S'-methylene-O,O,O',O'-tetraethyl ester; [(dimethoxyphosphinothioyl)-thio]-succinic acid diethyl ester; phosphoric acid 2-chloro-1-(2,4-dichlorophenyl)ethenyldiethyl ester; chlorinated camphene; 1α,2β,3β,4α,5α,6β-hexachlorocyclohexane; N-(2,3-dihydro-3-methyl-1,3-thiazol-2-ylidene)-2,4-xylidine or O-(α-cyanobenzylideneamino)-O',0''-diethyl thiophosphate.

11. A method according to claim 10, characterised in that thiophosphoric acid O,O-diethyl-O-[6-methyl-2-(1-methylethyl)-4-pyrimidinyl]ester is utilized as the ectoparasiticide.

12. A method of controlling ectoparasites in domestic animals which comprises the use of microencapsulated ectoparasiticides in animal dips in which used treatment liquid remains in the dip liquid or is fed back thereto.

13. The method according to claim 12, which comprises the use of microencapsulated ectoparasiticides according to claim 12 for reducing or preventing a stripping effect in dips for cattle, sheep, goats, horses, donkeys, camels, pigs, reindeer, caribou, buffalo, dogs and rabbits.

* * * * *